(12) United States Patent
Xue et al.

(10) Patent No.: US 11,598,832 B2
(45) Date of Patent: Mar. 7, 2023

(54) MAGNETIC RESONANCE SIGNAL TRANSMISSION LINE CONNECTION STRUCTURE AND MAGNETIC RESONANCE IMAGING DEVICE HAVING SAME

(71) Applicant: Siemens Healthcare GmbH, Erlangen (DE)

(72) Inventors: Ting Qiang Xue, Shenzhen (CN); JianMin Wang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/880,049

(22) Filed: May 21, 2020

(65) Prior Publication Data

US 2020/0371177 A1    Nov. 26, 2020

(30) Foreign Application Priority Data

May 22, 2019    (CN) .......................... 201910428843.4

(51) Int. Cl.
  *G01R 33/36*    (2006.01)
  *A61B 5/055*    (2006.01)

(52) U.S. Cl.
  CPC .......... *G01R 33/3692* (2013.01); *A61B 5/055* (2013.01); *G01R 33/3621* (2013.01); *G01R 33/3642* (2013.01)

(58) Field of Classification Search
  CPC ............ G01R 33/3692; G01R 33/3621; G01R 33/3642; A61B 5/055
  See application file for complete search history.

(56) References Cited

U.S. PATENT DOCUMENTS

| | | | | |
|---|---|---|---|---|
| 4,712,067 A * | 12/1987 | Roschmann | ..... | G01R 33/34046 324/318 |
| 5,450,011 A * | 9/1995 | Boeijen | .............. | G01R 33/3628 324/318 |
| 6,144,205 A * | 11/2000 | Souza | .................. | G01R 33/341 324/322 |
| 6,326,789 B1 * | 12/2001 | Yoshida | ............. | G01R 33/3415 324/307 |
| 6,750,653 B1 * | 6/2004 | Zou | ...................... | G01R 33/341 324/318 |
| 9,335,391 B2 * | 5/2016 | Takagi | ............... | G01R 33/3664 |
| 9,684,044 B2 * | 6/2017 | Habara | ............. | G01R 33/3453 |

(Continued)

*Primary Examiner* — Dixomara Vargas
(74) *Attorney, Agent, or Firm* — Banner & Witcoff Ltd.

(57) ABSTRACT

MR signal transmission line connection structure. A first connector fixed to a bed of an MR imager and connectable to an MR imaging. A second connector, which is disposed at an opposite side of an opening side of a chamber of the MR imaging device allowing entry of the bed, connected to a signal receiver for MR signals by a cable. The first connector has a first connection terminal, and the second connector has a second connection terminal. When the bed moves into the chamber, the first connector abuts the second connector such that the first connection terminal is connected to the second connection terminal, and an MR signal received by the coil is conveyable to the signal receiver via the first and second connection terminals. When the MR imaging ends, the bed moves back out of the chamber, breaking the connection between the first and second connection terminals.

7 Claims, 8 Drawing Sheets

(56) References Cited

U.S. PATENT DOCUMENTS

| | | | | |
|---|---|---|---|---|
| 2008/0015430 A1* | 1/2008 | Takamori | ........... | G01R 33/3415 |
| | | | | 600/415 |
| 2008/0030195 A1* | 2/2008 | Hagen | ................... | G01R 33/481 |
| | | | | 324/322 |
| 2008/0141461 A1* | 6/2008 | Feld | ....................... | A61B 5/055 |
| | | | | 5/601 |
| 2009/0027053 A1* | 1/2009 | Decke | .................... | A61B 5/055 |
| | | | | 324/318 |
| 2012/0059242 A1* | 3/2012 | Caruba | ................ | A61B 5/0035 |
| | | | | 600/411 |
| 2013/0176029 A1* | 7/2013 | Oosawa | ................. | A61B 5/055 |
| | | | | 324/321 |
| 2014/0253126 A1* | 9/2014 | Habara | .............. | G01R 33/3453 |
| | | | | 324/322 |
| 2014/0361769 A1* | 12/2014 | Hardie | ................... | G01R 33/34 |
| | | | | 324/307 |
| 2015/0168515 A1* | 6/2015 | Ishihara | ................ | A61B 5/055 |
| | | | | 324/322 |
| 2016/0077175 A1* | 3/2016 | Mori | .................... | G01R 33/307 |
| | | | | 324/321 |
| 2019/0310328 A1* | 10/2019 | Fuqua | ................ | G01R 33/3685 |

* cited by examiner

MAGNETIC RESONANCE SIGNAL TRANSMISSION LINE CONNECTION STRUCTURE AND MAGNETIC RESONANCE IMAGING DEVICE HAVING SAME

TECHNICAL FIELD

The present disclosure relates to a magnetic resonance signal transmission line connection structure, in particular a magnetic resonance imaging device having same.

BACKGROUND

The use of a local coil is essential for a patient lying on a patient bed. When receiving a signal from the patient's body, the local coil must transmit the complex signal via a cable to a signal receiver, and data resulting from signal conversion is then transmitted to an image reconstruction center. The patient's body will move together with the patient bed, therefore the local coil cable must also move relative to a magnetic resonance scanner.

FIG. 1 shows a schematic drawing of a magnetic resonance system in the prior art. The magnetic resonance system in the prior art comprises a system main body 1; a chamber 2 for a patient bed 3 and a patient to pass through is disposed in the system main body 1. In the situation shown here, the patient bed 3 and the patient enter the chamber 2 completely to perform an examination. At this time, a part of a patient bed cable 5 connected to a bed head end of the patient bed 3 is in the chamber 2. In order to reduce signal interference to ensure imaging quality, multiple RF chokes 6 are disposed on the patient bed cable 5, section by section, to eliminate external interference. Since the patient bed cable 5 must be wound in order to realize the RF choke 6, the external diameter of the RF choke is greater than the external diameter of the cable; as a result, the patient bed cable 5 is very long, and generally may reach 15 meters. The part of the patient bed cable 5 that is in the chamber 2 will suffer the greatest amount of external interference, and therefore must be provided with multiple RF chokes. In other situations requiring a greater number of RF reception channels, due to the increased number of cables, it is necessary to provide a greater number of RF chokes, so there is the problem of patient bed structural layout space being taken up.

Moving cables require very good treatment or protection, otherwise the cables might become jammed in the chamber and cause a blockage, such that the patient bed is unable to move. Since the cable has a certain hardness, and has a complex internal structure, existing cable treatment schemes are generally very expensive or dimensions are large.

In recent years, users have demanded that movable patient beds can be provided. In an existing movable patient bed, a plug of the cable of the patient bed must be reliably inserted into a socket 7 disposed in a lower region of the main body 1; since the plug of the cable must have multiple pins, the pins of the plug are bent easily in the process of inserting the plug into the socket or removing the plug therefrom, with the result that connection to the socket cannot be carried out smoothly.

SUMMARY

In view of the above, the present disclosure provides a magnetic resonance signal transmission line connection structure that is capable of reducing the magnetic resonance signal transmission line length and reducing the number of RF chokes used, and can be effectively used on a moving patient bed; the present disclosure also proposes an MRI system having same.

An embodiment of the present disclosure provides a magnetic resonance signal transmission line connection structure, comprising: a first connection part, fixed to a patient bed of a magnetic resonance imaging device and connectable to a coil which performs magnetic resonance imaging; a second connection part, disposed at another side, opposite an opening side allowing entry of the patient bed, of a chamber of the magnetic resonance imaging device, and connected to a signal receiver for magnetic resonance signals by means of a cable disposed at the other side; the first connection part having at least one first connection terminal, and the second connection part having at least one second connection terminal; when the patient bed moves into the chamber to perform magnetic resonance imaging, the first connection part abuts the second connection part, such that the first connection terminal is connected to the second connection terminal, and a magnetic resonance signal received by the coil can be conveyed to the signal receiver via the first connection terminal and the second connection terminal, and when magnetic resonance imaging ends, the patient bed moves back out of the chamber, breaking the connection between the first connection terminal and the second connection terminal.

In the magnetic resonance signal transmission line connection structure described above, preferably, the first connection terminal is a non-contact-type first coupling-connection terminal, the second connection terminal is a non-contact-type second coupling-connection terminal, and when the first connection part abuts the second connection part, the first coupling-connection terminal and the second coupling-connection terminal are connected by coupling.

In the magnetic resonance signal transmission line connection structure described above, preferably, the first connection terminal is a contact; the second connection terminal is a busbar, and when the patient bed moves into the chamber to perform magnetic resonance imaging, the contact abuts the busbar, and can slide on the busbar to maintain signal conduction.

In the magnetic resonance signal transmission line connection structure described above, preferably, the coil is a non-contact-type coupling-connection coil, and the first connection part further comprises a coupling terminal for coupling to the coil.

In the magnetic resonance signal transmission line connection structure described above, the coil may also employ a conventional plug/socket manner of connection, and the first connection part further comprises a socket for connection to the coil.

In the magnetic resonance signal transmission line connection structure described above, preferably, the second connection part is disposed on the magnetic resonance imaging device via a return mechanism, the second connection part being movable, and able to return to an initial position using the return mechanism.

In the magnetic resonance signal transmission line connection structure described above, preferably, the return mechanism is a spring, the spring having one end disposed on the magnetic resonance imaging device and another end connected to the second connection part via a fixed pulley.

In the magnetic resonance signal transmission line connection structure described above, preferably, the cable is accommodated in a cable drag chain.

The present disclosure further provides a magnetic resonance imaging device, comprising: a main body, having a hollow chamber; a patient bed, capable of moving relative to the chamber; and any one of the magnetic resonance signal transmission line connection structures described above.

According to the present disclosure, since the cable for transmitting magnetic resonance signals is located at a maintenance side of the MRI system main body (the side opposite a patient bed entry side), there is no need for a very long magnetic resonance signal transmission line, and a large number of correspondingly arranged chokes, to be arranged in the patient bed as in the prior art, thus it is possible to reduce the length of the magnetic resonance signal transmission line and the number of chokes used; at the same time, since there is no need for a transmission line for magnetic resonance signals to be configured in the patient bed, it is possible to simplify the patient bed structure, reduce the thickness of the patient bed, and reduce the risk of patient bed faults. Especially importantly, the magnetic resonance signal transmission line connection structure according to the present disclosure enables separate arrangement of the first connection part disposed on the patient bed and the second connection part disposed on the magnetic resonance main body, and is therefore especially favorable for the design of movable patient beds.

BRIEF DESCRIPTION OF THE DRAWINGS

Preferred embodiments of the present disclosure are described in detail below with reference to the accompanying drawings, to give those skilled in the art a clearer understanding of the abovementioned and other features and advantages of the present disclosure.

Figure 1:
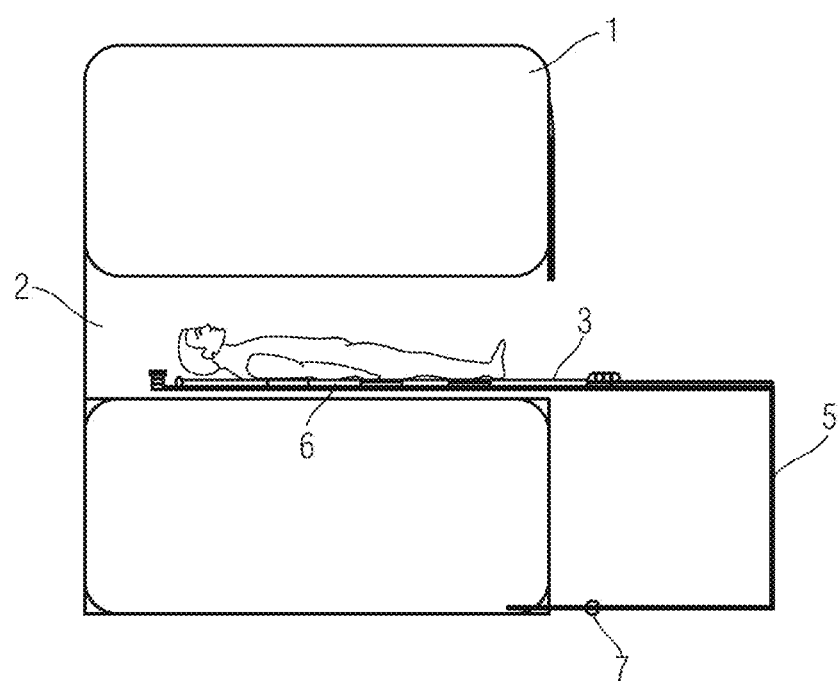
FIG. 1 is an illustrative diagram of an existing magnetic resonance signal transmission line and MRI system.

Key to the drawings:
1 main body
2 chamber
3 patient bed
4 coil
5 magnetic resonance signal transmission line connection structure
50, 50' first connection part
52, 52' second connection part
501, 502 coil terminal
503, 503' first connection terminal
521, 521' second connection terminal
53 cable

DETAILED DESCRIPTION

In the absence of conflict, embodiments in the present disclosure and features in embodiments can be combined with each other. The present disclosure is explained in detail below with reference to the drawings, in conjunction with embodiments.

Unless otherwise specified, all technical and scientific terms used in the present disclosure have the same meanings as those generally understood by those skilled in the art.

Unless specified otherwise, words relating to orientation which are used in the present disclosure such as "up, down, top and bottom" generally relate to the directions shown in the drawings, or relate to the components themselves in the vertical, perpendicular or gravity directions; similarly, to facilitate understanding and description, "inner and outer" mean inner and outer relative to the profile of each component itself. However, the abovementioned words relating to orientation are not intended to limit the present disclosure.

For conciseness, other conventional components of a magnetic resonance system, such as guide rollers for guiding the movement of the patient bed in the chamber, etc., have not been shown here.

Figure 2:
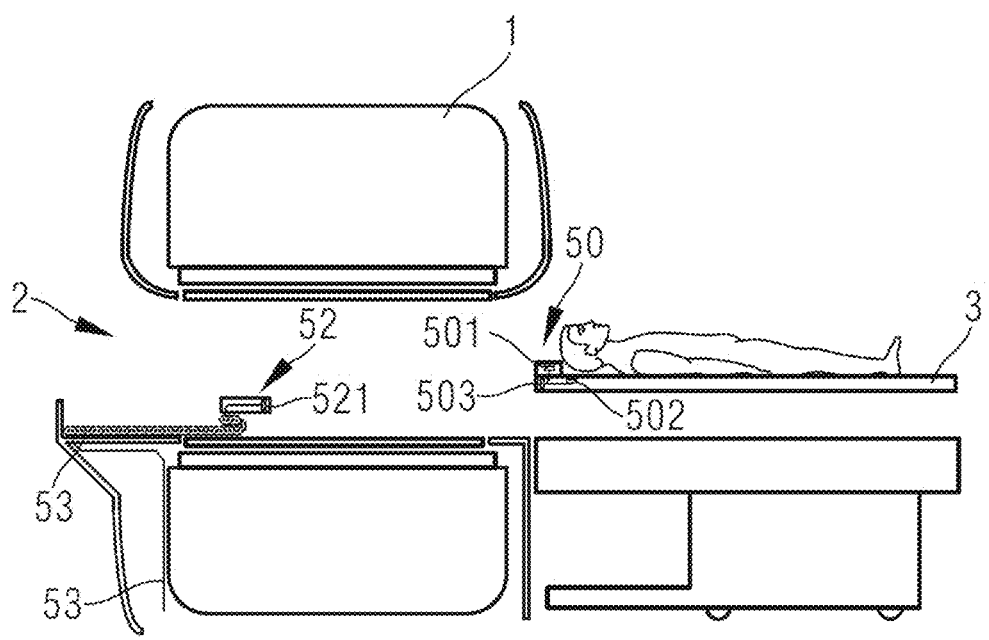
FIG. 2 shows a schematic diagram of an MRI system using a magnetic resonance signal transmission line connection structure of the present disclosure, wherein a return mechanism part of a second connection part is omitted from the second connection part.
Figure 3:
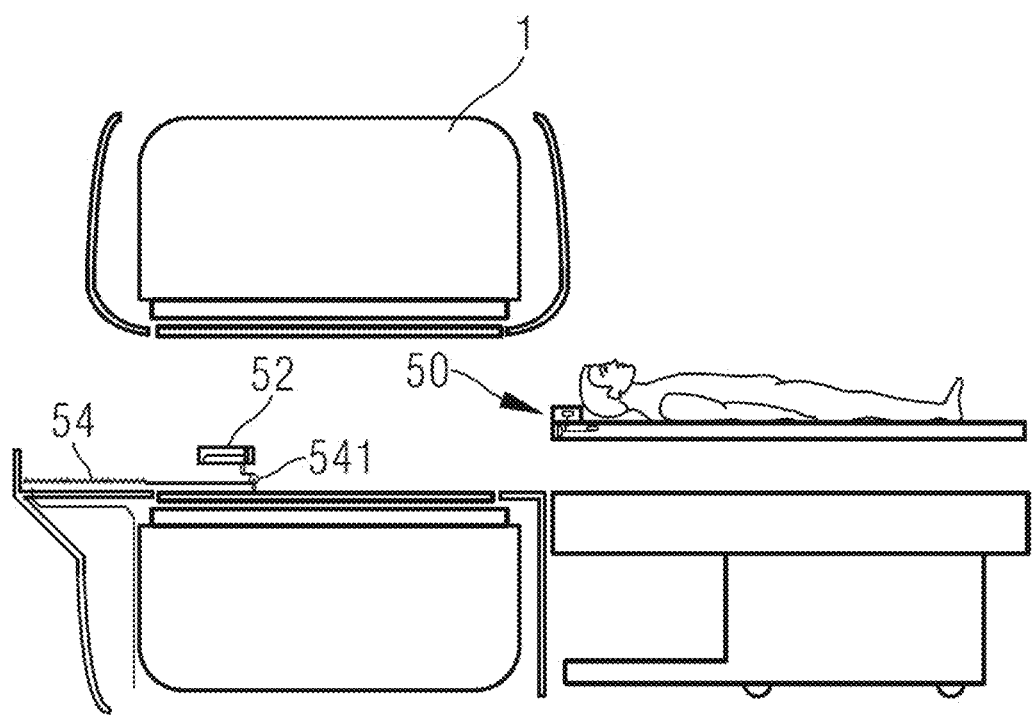
FIG. 3 shows a schematic diagram of the MRI system corresponding to the magnetic resonance signal transmission line connection structure of FIG. 2, wherein a coil cable part is omitted from the second connection part.
Figure 4:
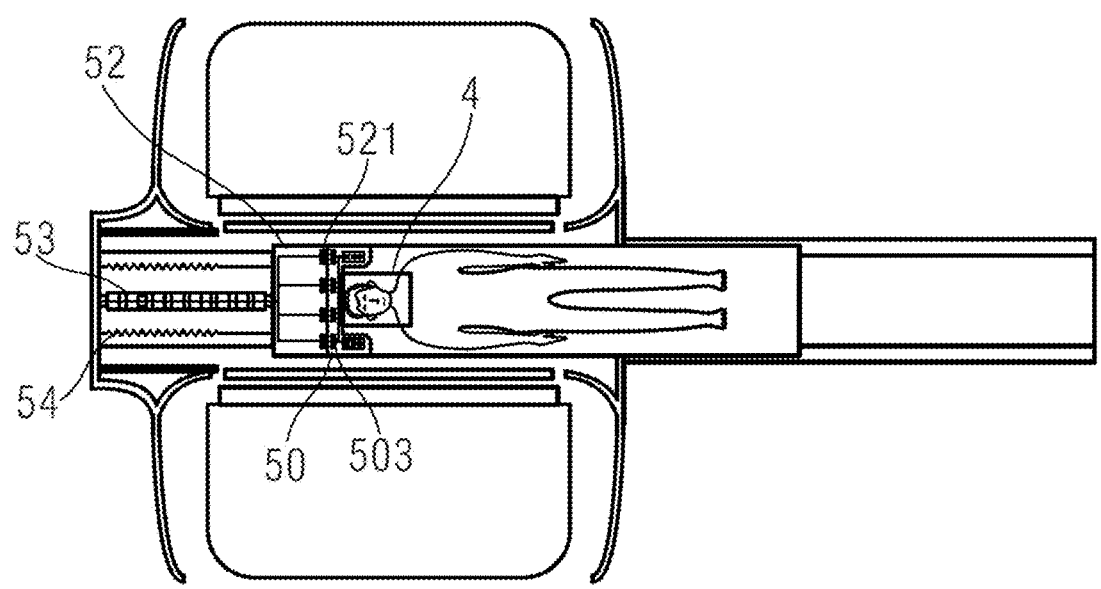
FIG. 4 shows a state diagram of a coil being used to perform magnetic resonance imaging of a head.

FIG. 2 shows a schematic diagram of an MRI system using an embodiment of a magnetic resonance signal transmission line connection structure 5 of the present disclosure. FIG. 3 shows a magnetic resonance signal transmission line connection structure 5 corresponding to FIG. 2, wherein a coil cable part is omitted from a second connection part. FIG. 4 shows a state diagram of a head coil being used to perform magnetic resonance imaging. In FIG. 2, the MRI system comprises: a main body 1, having a hollow chamber 2; a patient bed 3, which is movable relative to the chamber 2; and the magnetic resonance signal transmission line connection structure 5. The magnetic resonance signal transmission line connection structure 5 comprises a first connection part 50 disposed on the patient bed 3, and a second connection part 52 disposed at a maintenance side of the system main body 1 of the MRI system; here, the maintenance side generally means the side at which maintenance operations are performed on the MRI system, i.e. the other side opposite the side at which the patient bed 3 enters the chamber 2.

In this embodiment, as shown in FIG. 2, the first connection part 50 is disposed at an end F, which can move into the chamber 2 first, of the patient bed 3. The first connection part 50 comprises terminals 501 and 502 connected to a local coil 4 for receiving a magnetic resonance signal, wherein terminal 501 is a socket-type terminal, and terminal 502 is a non-contact-type coupling terminal. In addition, the first connection part 50 further comprises at least one first connection terminal 503 for engaging with the opposite second connection part 52 (described in detail below). In this embodiment, the first connection terminal is shown as a non-contact-type first coupling-connection terminal by way of example, but is not limited to this; it may also be a contact-type first contact terminal as mentioned below. In the first connection part 50, terminals 501 and 502 are separately connected to the first connection terminal 503.

The second connection part 52 is movably disposed at the maintenance side of the system main body 1 of the MRI system, i.e. the other side opposite the side at which the patient bed 3 enters the chamber 2, and is connected from the maintenance side to a signal receiver (not shown) of the MRI device via a cable 53. The second connection part 52 comprises at least one second connection terminal 521 for connecting to the first connection terminal 503, and the cable 53 connected to the second connection terminal 521. In this embodiment, the second connection terminal 521 is shown as a non-contact-type second coupling-connection terminal by way of example, but is not limited to this; it may also be a contact-type second contact terminal as mentioned below. In addition, this embodiment shows by way of example the use of a drag-chain cable as the cable 53 to transmit magnetic resonance signals; the use of a drag-chain cable can ensure that when the second connection part 52 is moving, undesirable situations such as cable tangling will not occur. However, there is no limitation to this; all that is needed is a cable that is able to transmit magnetic resonance signals.

In addition, as shown in FIG. 3, the second connection part 52 in this embodiment is disposed in an initial position in the MRI device main body 1 by means of a spring 54 (a return mechanism). The spring 54 is disposed at two sides of the cable 53 respectively (see FIG. 4); the spring 54 has one end fixed to the device main body 1, and another end connected to the second connection part 52 via a fixed pulley 541. Using the fixed pulley 541, it is possible to shorten the travel of the spring 54 when the second connection part 52 moves, and it is thereby possible to use a smaller spring, making the structure more compact.

FIG. 4 shows a state diagram of the magnetic resonance signal transmission line connection structure 5 of this embodiment being used, when a non-contact-type coil 4 is used to perform head imaging. As shown in FIG. 4, the patient bed 3 is conveyed into the chamber 2, until the coil 4 is located at the center of an imaging region, such that the first connection part 50 disposed at one end of the patient bed 3 abuts the second connection part 52 located in the chamber 2; at this time, multiple first coupling-connection terminals 503 disposed in the first connection part 50 can couple with multiple second coupling-connection terminals 521 disposed in the second connection part 52. Here, the first connection part 50 is shown as comprising four non-contact-type first coupling-connection terminals 503 by way of example, each first coupling-connection terminal 503 being connectable to a coil unit in the coil 4, and correspondingly, the second connection part 52 comprises four non-contact-type second coupling-connection terminals 521. When a patient is imaged using the non-contact-type coil 4, a coupling output terminal 41 of the coil 4 is coupled to the coupling terminal 502 of the first connection part 50; thus, magnetic resonance signals received from each coil unit in the coil 4 can be coupled to the first connection part 50 via the coupling terminal 502, and coupled to the second connection part 52 via the first coupling-connection terminal 503, and then transmitted via the cable 53 to the magnetic resonance signal receiver for processing.

Figure 5:
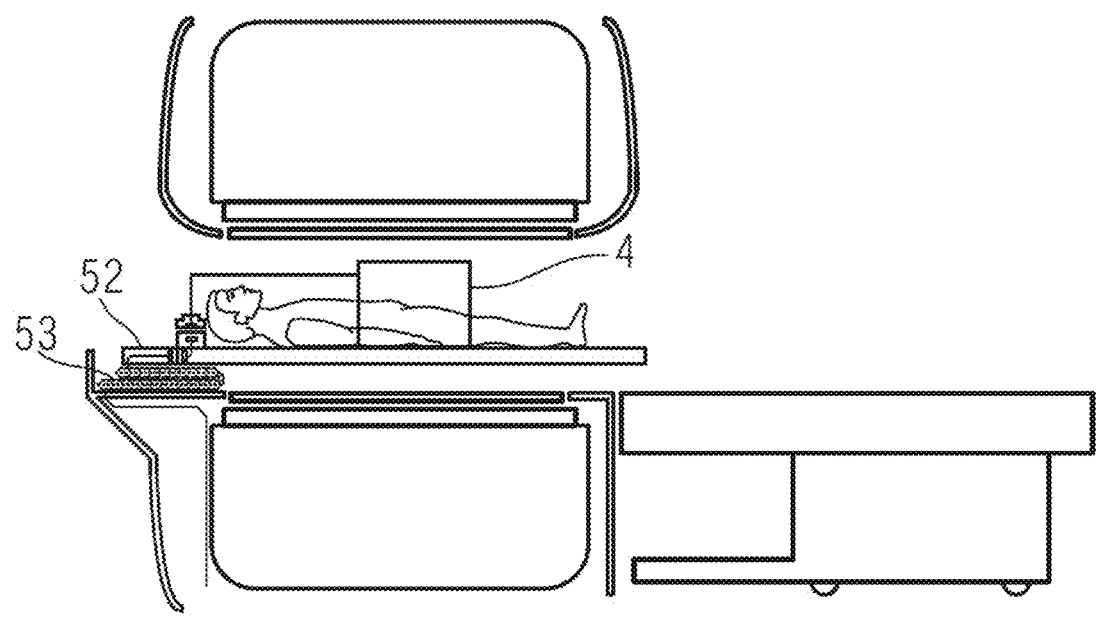
FIG. 5 shows a state diagram of a cable when a patient's abdomen is being imaged using a coil.
Figure 6:
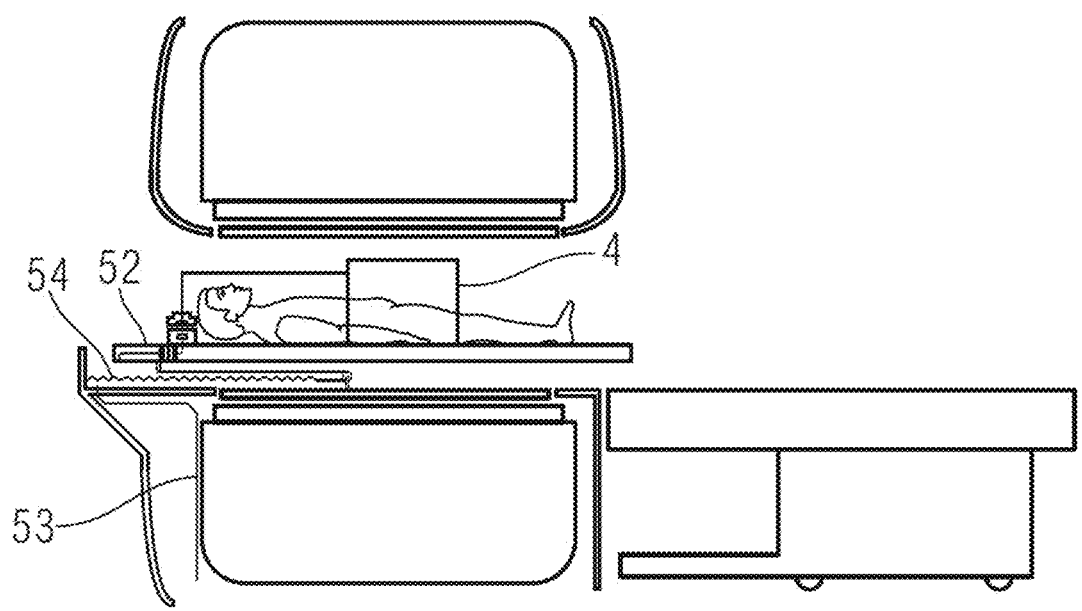
FIG. 6 shows a state diagram of a spring when a patient's abdomen is being imaged using a coil.

FIGS. 5 and 6 show state diagrams of the cable 53 and the spring 54 respectively when the patient's abdomen is being imaged using the coil 4. As shown in FIG. 5, when the abdomen is imaged, compared with imaging of the head, the patient bed 3 must move further toward the maintenance side of the MRI device (the side opposite the patient bed entry side), so that the patient's abdomen can be located at the center of the imaging region of the chamber 2. In this state, the first connection part 50 disposed at one end of the patient bed 3 pushes the second connection part 52 located in the chamber 2 further toward the side opposite the patient bed entry side, such that the second connection part 52 moves toward the abovementioned opposite side together with the cable 53. At this time, as shown in FIG. 6, the springs 54 located at two sides of the cable 53 are stretched, giving rise to an elastic force causing the second connection part 52 to return to the initial position. When scanning imaging ends, the patient bed 3 returns to the patient bed entry side of the chamber 2, and at the same time, the second connection part 52 returns to the initial position under the action of the elastic force of the springs 54.

The embodiment above shows by way of example the use of a non-contact coupling-type coil, and the use of non-contact coupling-type coupling-connection terminals in the first and second connection parts, but there is no limitation to this; a contact-type manner of connection may also be used.

Figure 7:
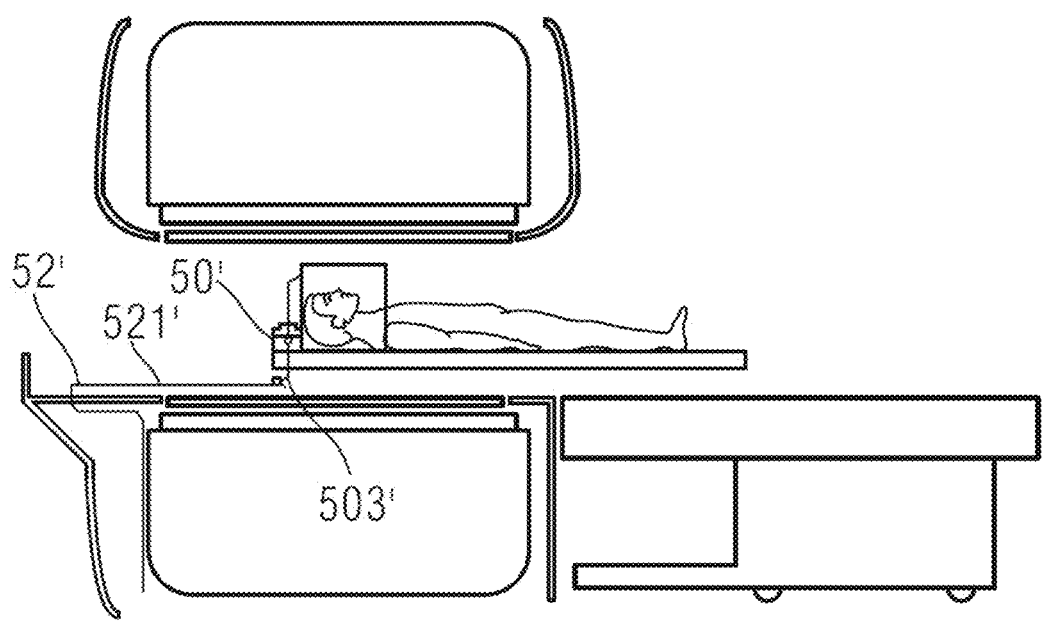
FIG. 7 shows a side sectional view of another embodiment in which a contact-type coil is used, and contact-type connection terminals are used in first and second connection parts.
Figure 8:
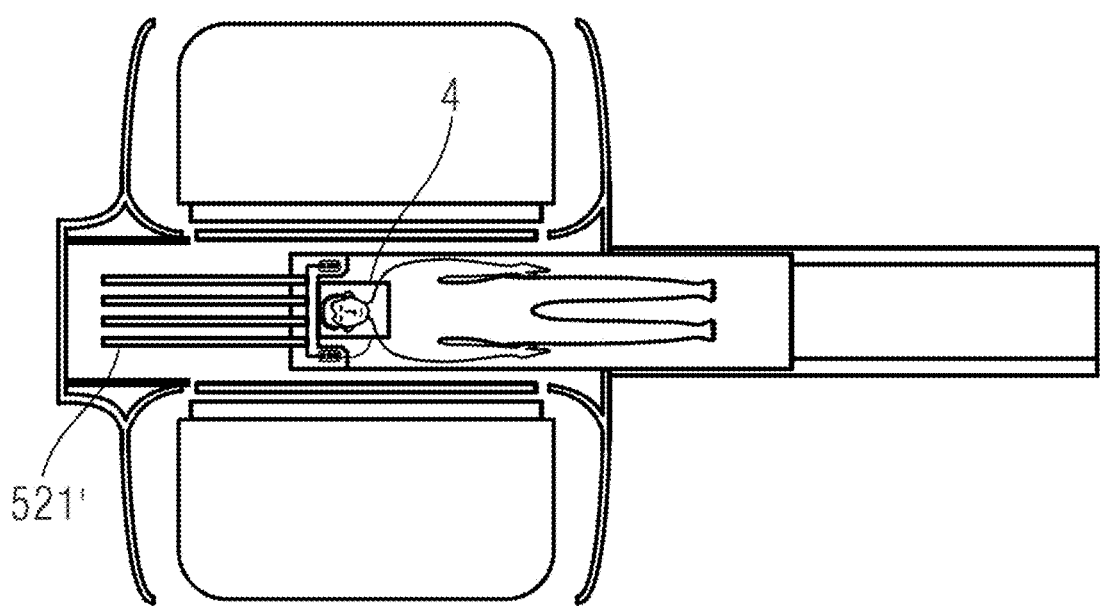
FIG. 8 shows a top view of another embodiment in which a contact-type coil is used, and contact-type connection terminals are used in first and second connection parts.

FIGS. 7 and 8 show illustrative diagrams of the use of a contact-type coil, and the use of contact-type connection terminals in the first and second connection parts. As shown in FIG. 7, a coil 4 is inserted into a socket-type terminal 501 of a first connection part 50' by means of a connection line; the first connection part 50' further comprises a contact-type contact 503', which serves as a first connection terminal and is configured to be connected to a second connection part 52'. The second connection part 52' is fixed at the maintenance side of the main body 1 of the MRI system, i.e. the other side opposite the side at which the patient bed 3 enters the chamber 2. However, unlike the embodiment above, the second connection part 52' comprises a busbar 521', which serves as a second connection terminal and is configured to come into contact with the contact 503'. As shown in FIG. 8, when the patient is imaged, the moving patient bed causes the coil 4 to move to the center of the imaging region; at this time, the contact 503' of the first connection part 50' can be in sliding contact with the busbar 521' of the second connection part 52'. Thus, a magnetic resonance signal received by the coil 4 can be inputted to the first connection part 50' via the terminal 501, and inputted to the busbar 521' of the second connection part 52' via the contact 503', and then inputted to the magnetic resonance signal receiver via the cable 53 connected to the busbar 521'. In this embodiment, there is no need for a return mechanism such as a spring, so the structure can be simplified.

According to the embodiment above, since the cable for transmitting magnetic resonance signals is located at the maintenance side of the MRI system main body (the side opposite the patient bed entry side), there is no need for a very long magnetic resonance signal transmission line, and a large number of correspondingly arranged chokes, to be arranged in the patient bed as in the prior art, thus it is possible to reduce the length of the magnetic resonance signal transmission line and the number of chokes used; at the same time, since there is no need for a transmission line for magnetic resonance signals to be configured in the patient bed, it is possible to simplify the patient bed structure, reduce the thickness of the patient bed, and reduce the risk of patient bed faults. Especially importantly, the magnetic resonance signal transmission line connection structure according to the present disclosure enables separate arrangement of the first connection part disposed on the patient bed and the second connection part disposed on the magnetic resonance main body, and is therefore especially favorable for the design of movable patient beds.

In the embodiments above, four non-contact-type first/second coupling-connection terminals or four contact-type contacts and a busbar have been shown by way of example, but there is no limitation to this; the number may also be greater.

In addition, the use of a non-contact coupling-type coil and non-contact coupling-type connection terminals of the first and second connection parts has been shown by way of example in the first embodiment above, and the second embodiment has shown a contact-type coil and contact-type terminals of the first and second connection parts by way of example, but those skilled in the art will of course know that the non-contact coupling-type coil in the first embodiment above may of course also be used in combination with the contact-type terminals of the first and second connection parts in the second embodiment, or the contact-type coil in the second embodiment above may also be used in combination with the non-contact-type coupling terminals of the first and second connection parts in the first embodiment.

The embodiments above are merely preferred embodiments of the present disclosure, which are not intended to limit it. Any amendments, equivalent substitutions or improvements etc. made within the spirit and principles of the present disclosure shall be included in the scope of protection thereof.

The invention claimed is:

1. A magnetic resonance signal transmission line connection structure, comprising:
a first connector fixed to a patient bed of a magnetic resonance imaging device and connectable to a coil configured to perform magnetic resonance imaging; and
a second connector, which is movably disposed at an opposite side of an opening side of a chamber of the magnetic resonance imaging device allowing entry of the patient bed, is connected to a main body of the magnetic resonance imaging device, and is connected to a signal receiver for magnetic resonance signals by a cable disposed at the other side,
wherein the first connector has at least one first connection terminal that is a non-contact-type first coupling-connection terminal, and the second connector has at least one second connection terminal that is a non-contact-type second coupling-connection terminal, and
wherein when the patient bed moves into the chamber to perform magnetic resonance imaging, the first connector abuts the second connector such that the first coupling-connection terminal is connected by coupling to the second coupling-connection terminal, and a magnetic resonance signal received by the coil is conveyable to the signal receiver via the first connection terminal and the second connection terminal, and when magnetic resonance imaging ends, the patient bed is moves back out of the chamber, breaking the connection between the first connection terminal and the second connection terminal.

2. The magnetic resonance signal transmission line connection structure as claimed in claim 1, wherein the coil is a non-contact-type coupling-connection coil, and the first connector further comprises a coupling terminal configured to couple to the coil.

3. The magnetic resonance signal transmission line connection structure as claimed in claim 1, wherein the coil has a plug/socket manner of connection, and the first connector comprises a socket for connection to the coil.

4. The magnetic resonance signal transmission line connection structure as claimed in claim 1, wherein the second connector is disposed on the magnetic resonance imaging device via a return mechanism, and the second connector is movable and able to return to an initial position using the return mechanism.

5. The magnetic resonance signal transmission line connection structure as claimed in claim 4, wherein the return mechanism is a spring having one end disposed on the magnetic resonance imaging device and another end connected to the second connector via a fixed pulley.

6. The magnetic resonance signal transmission line connection structure as claimed in claim 1, wherein the cable is accommodated in a cable drag chain.

7. A magnetic resonance imaging device, comprising:
a main body having a hollow chamber;
a patient bed movable relative to the chamber; and
a magnetic resonance signal transmission line connection structure comprising:
a first connector fixed to a patient bed of a magnetic resonance imaging device and connectable to a coil configured to perform magnetic resonance imaging; and
a second connector, which is movably disposed at an opposite side of an opening side of the chamber of the magnetic resonance imaging device allowing entry of the patient bed, is connected to a main body of the magnetic resonance imaging device, and is connected to a signal receiver for magnetic resonance signals by a cable disposed at the other side,
wherein the first connector has at least one first connection terminal that is a non-contact-type first coupling-connection terminal, and the second connector has at least one second connection terminal that is a non-contact-type second coupling-connection terminal, and
wherein when the patient bed moves into the chamber to perform magnetic resonance imaging, the first connector abuts the second connector such that the first coupling-connection terminal is connected by coupling to the second coupling-connection terminal, and a magnetic resonance signal received by the coil is conveyable to the signal receiver via the first connection terminal and the second connection terminal, and when magnetic resonance imaging ends, the patient bed moves back out of the chamber, breaking the connection between the first connection terminal and the second connection terminal.

\* \* \* \* \*